(12) United States Patent
Faccioli

(10) Patent No.: US 8,795,281 B2  
(45) Date of Patent: Aug. 5, 2014

(54) EQUIPMENT FOR REMOVING CEMENT FROM BONE CAVITIES

(75) Inventor: Giovanni Faccioli, Monzambano (IT)

(73) Assignee: Tecres S.p.A., Sommacapagna (IT)

( * ) Notice: Subject to any disclaimer, the term of this patent is extended or adjusted under 35 U.S.C. 154(b) by 1558 days.

(21) Appl. No.: 11/822,289

(22) Filed: Jul. 3, 2007

(65) Prior Publication Data

US 2008/0009879 A1 Jan. 10, 2008

(30) Foreign Application Priority Data

Jul. 4, 2006 (EP) .................................. 06425458

(51) Int. Cl.
*A61B 17/88* (2006.01)

(52) U.S. Cl.
USPC .............................. 606/86 R; 606/53; 606/92

(58) Field of Classification Search
USPC ........... 606/86 R, 99–100, 53, 62, 63, 87, 92, 606/95; 623/22.12, 23.19, 23.2, 23.48, 623/66.1, 908
See application file for complete search history.

(56) References Cited

U.S. PATENT DOCUMENTS

| 4,919,153 A | 4/1990 | Chin |
| 5,078,718 A * | 1/1992 | Moll et al. .................. 606/86 R |
| 2004/0111089 A1 * | 6/2004 | Stevens et al. .................. 606/69 |

FOREIGN PATENT DOCUMENTS

EP 0520293 12/1992

* cited by examiner

*Primary Examiner* — Michael T Schaper  
(74) *Attorney, Agent, or Firm* — Tutunjian & Bitetto, P.C.

(57) ABSTRACT

The equipment for removing cement from bone cavities consists of an elongated body, hollow inside, that can be inserted inside a cement-filled bone cavity, and at least one rod for extracting the elongated body buried in the cement, that can be inserted inside the elongated body. The elongated body comprises a plurality of rigid elements aligned with each other and associated to one another by the interposition of spacer elements, tubular in shape and coaxial to the elongated body, the rigid elements including removable means for connecting to the extraction rod which are arranged inside the elongated body.

18 Claims, 2 Drawing Sheets

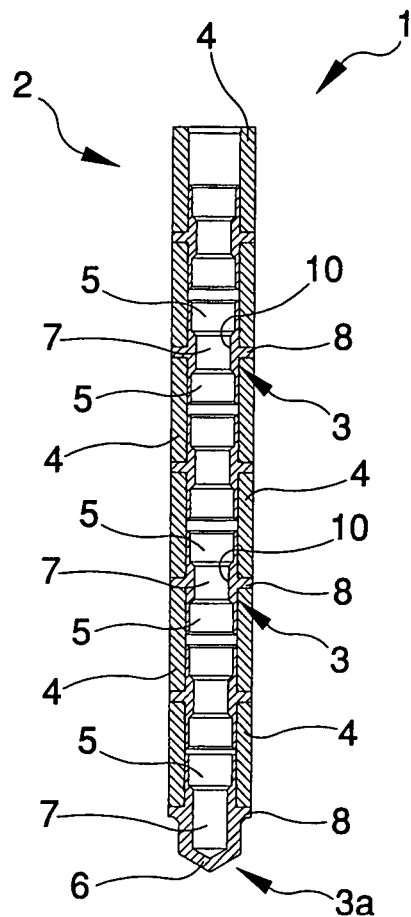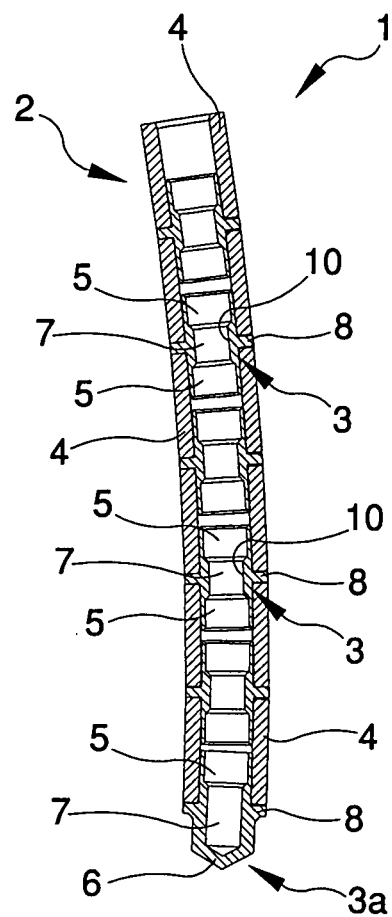
Fig. 1　　　Fig. 2
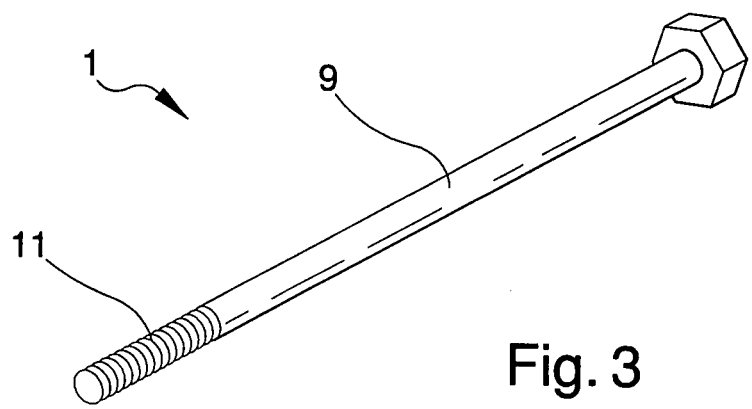
Fig. 3

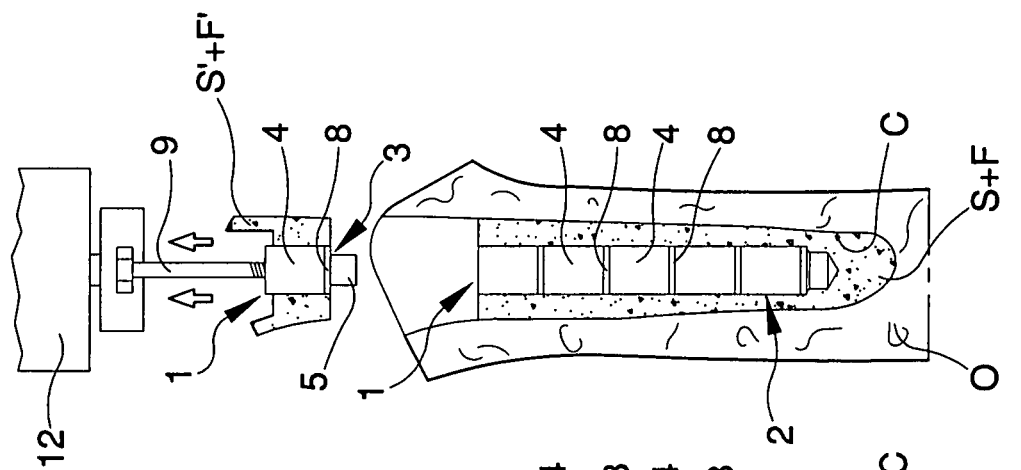
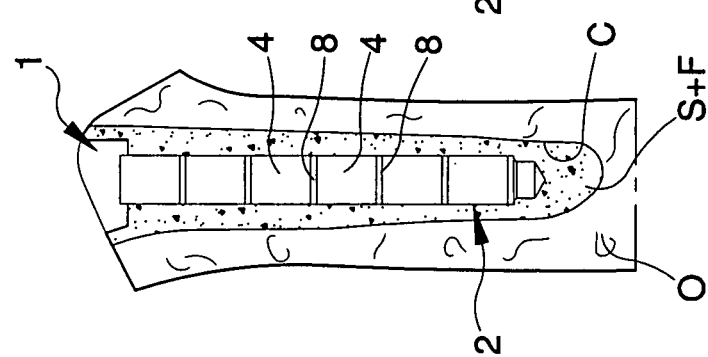
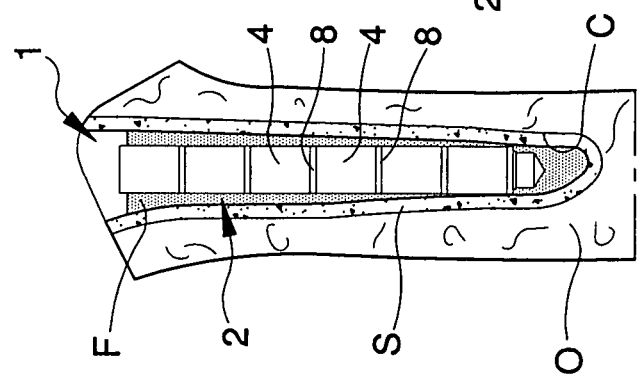
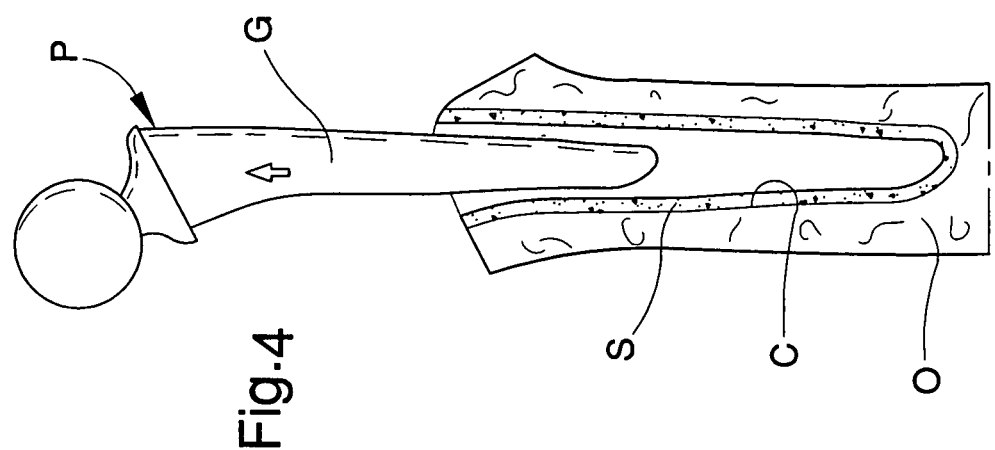

EQUIPMENT FOR REMOVING CEMENT FROM BONE CAVITIES

The present invention refers to an equipment for removing cement from bone cavities.

As is common knowledge, arthroplasty requiring the application of a prosthetic inside a bone normally needs a certain quantity of cement (acrylic resins or the like) to keep the prosthesis permanently in place.

In the case of a hip prosthesis for example, an elongated cavity is made at the proximal end of the femoral bone inside which the stem of the prosthesis is placed on top of a layer of liquid cement which, once set, fixes the prosthetic to the internal walls of the cavity.

When removing the prosthesis to replace it or for other medical/surgical operations where the prosthesis is located, the prosthesis is usually removed by simply exerting sufficient extraction force, leaving a hollow in the hardened cement which later needs to be removed from the bone cavity.

There are different known methods for extracting the hardened cement from a bone cavity.

One of such methods entails the use of an ultrasound instrument fitted with a spoon-shaped electrode.

The electrode is inserted by hand in the cavity and the heat created by the ultrasounds softens the hardened cement resin which can then be removed from the bone cavity by the spoon-shaped electrode.

This ultrasound instrument does have a few drawbacks, one being that it is particularly arduous and not very practical for the person using it who is obliged to manipulate the spoon-shaped electrode in a really tiny space as are the cavities normally made in femoral bones.

Moreover, inconveniently this job has to be done by highly specialized medical personnel with sufficient experience and skill.

And we ought not forget either that using a warming electrode near the inside walls of the bone does add the risk of heating the bone too much with the danger, as is well known, of compromising its sturdiness and state of health. To limit such a drawback, these ultrasound instruments are usually fitted with a sound device that warns the operator when he is getting near the walls of the bone; the efficiency of such devices however, is normally rather limited and does not make the use of ultrasounds risk free.

Another drawback with this technique is the high cost, from an energy point of view, and the overall cost which is not negligible.

Yet another technique to extract cement from bone cavities is described in the U.S. Pat. No. 4,919,153 and consists of injecting a liquid mass of fresh cement inside the bone cavity directly in contact with the layer of hardened cement left after the prosthesis has been extracted, sinking a shaped rod (with an irregular outer surface) in the fluid mass, leaving the liquid mass to harden and adhere to the rod and lastly exerting an extraction force to remove the rod from the bone cavity together with the cement.

Neither is this technique without drawbacks like, for instance, the fact that quite a considerable force is needed to remove all hardened cement from inside the cavity in one go, with the risk of over stressing the bone of the person being operated on.

To overcome this problem, the U.S. Pat. No. 5,078,718 describes a method similar to the previous one, differing in that the object inserted in the liquid cement mass is an elongated sleeve consisting of different longitudinal portions, separate from each other and held together by a removable internal screw.

Once the liquid cement mass has hardened and the sleeve has become one with it, the internal screw is removed and then the various longitudinal portions of the sleeve are extracted selectively, starting with the one closest to the proximal end of the femoral bone, and in this way level after level of cement is removed. Although this technique does mean we are free from the drawbacks described previously for the well known technique, it is not always simple and practical to use and still needs improving.

On the other hand, in the EP 0 520 293 a similar method is described for extracting cement using a threaded rod to which some nuts are screwed along its length, spaced one from the other.

The threaded rod is sunk into the fresh cement together with the nuts. After the cement has hardened, the rod is extracted, turning it around its own axis while the nuts remain buried in the hardened cement at different depths.

Lastly, using suitable extraction screws, the nuts are extracted one by one, bringing with them the various longitudinal portions of cement.

But this extraction system also has its drawbacks like, for instance, the fact that it takes a lot of manual work to prepare the threaded rod on which the nuts are fitted one at a time, necessary for extraction.

And we must not forget either that there can be some really serious complications and problems if it is difficult to pull the threaded rod out of the hardened cement.

If the threaded rod remains blocked in the cement, in fact, the space inside the bone cavity is completely filled with hardened cement and the threaded rod, leaving no room at all for removing the cement gradually from the outside; in such circumstances, it is often necessary to physically open the femoral bone, with extremely serious consequences for the patient.

We would also like to point out that in using these three techniques deriving from the U.S. Pat. Nos. 4,919,153, 5,078, 718 and EP 0 520 293, we often have cases where, after extraction, some hardened cement still remains in the bone cavity, conventionally called a "distal plug".

This distal plug is removed by subsequent supplementary operations where a hole is drilled in the plug, a self-tapping screw is then inserted in this hole and pulled out together with the plug.

These additional operations can be particularly inconvenient and not very practical, especially when drilling the distal plug.

As a matter of fact, to drill the distal plug correctly and without danger for the patient it is necessary to inconveniently use a twist-proof centring bush. The primary aim of this invention is to make a tool that will remove cement from bone cavities without any of the above mentioned drawbacks of the well known technique, with a simple, rational and cost-effective solution.

Another purpose of this invention is to extract cement from bone cavities in a practical and easy way for the operator doing the job and under conditions of maximum safety and ease of mind for the patient.

The aim and purposes described above are all achieved with this equipment for removing cement from bone cavities, comprising an elongated body, hollow inside, that can be inserted inside a cement-filled bone cavity, and at least one rod for extracting said elongated body buried in the cement, that can be inserted inside said elongated body, characterised by the fact that said elongated body comprises a plurality of rigid elements aligned with each other and associated to one another by the interposition of spacer elements, substantially tubular in shape and coaxial to said elongated body, said rigid elements including removable means for connecting to said extraction rod which are arranged inside said elongated body.

Further characteristics and advantages of this invention will appear even more evident from the detailed description of a preferred, but not exclusive, form of embodiment of an equipment for removing cement from bone cavities, illustrated by way of non limiting example in the accompanying drawings, wherein:

FIG. 1 is a longitudinal section view showing the elongated body of the equipment, according to the invention, arranged in a straight configuration;

FIG. 2 is a longitudinal section view of the elongated body of FIG. 1, arranged in a curved configuration;

FIG. 3 is a perspective view showing the extraction rod of the equipment according to the invention;

FIG. 4 is a section view of a bone cavity during removal of a hip prosthesis;

FIG. 5 is a section view of the bone cavity of FIG. 4 while filling with liquid cement and immersing the elongated body of the equipment according to the invention;

FIG. 6 is a section view of the bone cavity of FIG. 4 while hardening of the liquid cement and adhering to the elongated body of the equipment according to the invention;

FIG. 7 is a section view of the bone cavity of FIG. 4 during removal of a first portion of hardened cement.

With special reference to the above figures, a femoral bone at whose proximal end we find a bone cavity C has been generally designated by reference letter O. The bone cavity C is used for application of stem G of a hip prosthesis P by interposing a layer of cement S in the known way.

Once prosthesis G is removed, the bone cavity C is covered with a layer of hardened cement S and can be filled with fresh cement F.

The fresh cement F partially softens the layer of cement S and, if left to harden, becomes one with the layer of cement S.

This mass of hardened cement S+F thus formed can be removed by the equipment 1 according to this invention.

In particular, this equipment comprises an elongated body 2, hollow inside and with a circular section, which can be inserted inside the bone cavity C for sinking into the fresh cement F.

The elongated body 2 consists of a plurality of rigid elements 3, 3a in metal, aligned with each other and associated to one another by the interposition of spacer elements 4 tubular in shape and coaxial to said elongated body.

In detail, the rigid elements 3, 3a are associated to the spacer elements 4 by interposing a temporary fit-in type coupling so that the rigid elements 3, 3a and spacer elements 4 can be joined as long as there is no axial separation force exerted between them of an established extent.

Several connecting links 5, substantially tubular in shape, are used for this coupling, associated to the rigid elements 3, 3a and which can be fitted inside the open ends of the spacer elements 4.

More specifically, each rigid element 3, except for 3a arranged at the distal end of the elongated body 2, features a pair of connecting links 5, positioned at the opposite axial ends of the rigid element 3 respectively.

On the other hand, the rigid element 3a arranged at the distal end of the elongated body 2 has just one connecting link 5 and features a closed bottom wall 6 whose outer surface is slightly pointed and conical in shape. Usefully, the inside diameter of the spacer elements 4 and the outside diameter of the connecting links 5 is such to allow insertion of the connecting links 5 in the spacer elements 4, leaving very little play between them.

In actual fact, such a coupling matches sufficiently to impede fresh cement F getting between the rigid elements 3, 3a and the spacer elements 4 and therefore guarantees that the volume inside the elongated body 2 is always free while the cement is hardening.

At the same time, such a coupling allows limited mobility of the spacer elements 4 around the rigid elements 3, 3a so the elongated body 2 can be modelled by hand to follow the shape of the bone cavity C and the rigid elements 3, 3a and spacer elements 4 can be positioned along the straight axis (configuration illustrated in FIG. 1) and along the curved axis (configuration illustrated in FIG. 2).

Usefully, each rigid element 3, 3a has a reinforced ring shaped central body 7, from where the connecting links 5 extend coaxially, and a protrusion on the outer side, protruding crossways to the axis of the elongated body 2.

This crossways protrusion consists of a discoidal body 8, coaxial to the elongated body 2, on which the circular edges rest of the spacer elements 4 coupled to the connecting links 5.

The side extension of the discoidal bodies 8 is substantially equal to the thickness of the spacer elements 4 so, where the join is between the rigid elements 3, 3a and the spacer elements 4, the external side surface of the elongated body 2 is substantially smooth, with no significant protrusions or grooves.

The elongated body 2 also has attaching means for connecting to the mass of hardened cement S+F inside the bone cavity C.

Such attaching means are of the adhesive type and consist of the same spacer elements 4.

As a matter of fact, the spacer elements 4 are made of a material that adheres firmly to the mass of hardened cement S+F. This material is made, for example, of an acrylic resin with a polymethylacrylate base or of a substance similar to the resins usually employed as bone cements.

The equipment 1 also has a rod 9 for extracting the elongated body 2 once the latter, buried in the fresh cement F, has adhered to the mass of hardened cement S+F.

The extraction rod 9 can be inserted along the elongated body 2 and is associated to the rigid elements 3, 3a which, for this purpose, are fitted internally with removable means for connecting to the rod.

Said means for connecting are threaded and comprise an internal screw 10 which is made in the inner surface of the reinforced central bodies 7, extending coaxially to the axis of the elongated body 2, with an external thread 11 at the distal end of the extraction rod 9 engaging with it.

In detail, the external thread 11 extends along the extraction rod 9 for a length substantially less than the distance defined between two consecutive internal screws 10 so that it cannot engage two or more rigid elements 3, 3a simultaneously.

The operation of this invention is the following.

During the preliminary phases of the operation on the patient, the operator can manually model the elongated body 2 to fit the type of bone cavity C in which it is going to be inserted, configuring it along a straight or curved axis or a combination of both.

Once the hip prosthesis P (FIG. 4) has been extracted, the recess left by stem G of the prosthesis is filled with fresh cement F.

At this point the elongated body 2 is sunk into the fresh cement F (FIG. 5) and left until the fresh cement F has hardened completely, adhering firmly to the hardened layer of cement S and to the spacer elements 4 of the elongated body 2 (FIG. 6).

Subsequently, the extraction rod 9 is inserted inside the elongated body 2 and the external thread 11 is screwed into the internal screw 10 of the first rigid element 3 positioned at the proximal end of the elongated body 2.

With a hammer device 12, of the known type, a tractive type of impact force is exerted on the extraction rod 9 which, through the rigid element 3 arranged at the proximal end of the elongated body 2, is transmitted to the spacer element 4 immediately higher up and to portion S'+F' of the mass of hardened cement S+F that is around it.

As a result of this impact force, the S'+F' portion of cement is separated from the rest of the mass of hardened cement S+F and, hence, extracted from the bone cavity C (FIG. 7).

By repeating this for each of the rigid elements 3, 3a sunk in the cement, all, or almost all the mass of hardened cement S+F can be removed.

Note that once the rigid element 3a arranged at the distal end of the elongated body 2 has been extracted, there could still be a distal plug of hardened cement left at the bottom of the bone cavity C; it can be removed using traditional techniques of drilling and extracting with a self-tapping screw.

In such a case, the particular shape of the rigid element 3a at the distal end of the elongated body 2 and of the conical surface of the bottom wall 6 impresses a hollow shape on the distal plug that centres the drill bit, making it much easier to remove the plug.

It has in fact been found that the described invention achieves the intended purposes.

The invention thus conceived is susceptible of numerous modifications and variations, all of which falling within the scope of the inventive concept. Furthermore all the details can be replaced with others that are technically equivalent.

In practice, the materials used, as well as the shapes and dimensions, may be any according to requirements without because of this moving outside the protection scope of the following claims.

The invention claimed is:

1. Equipment for removing bone cement from bone cavities, comprising an elongated body, hollow inside, that can be inserted inside a cement-filled bone cavity, and at least one extraction rod for extracting said elongated body buried in the cement, that can be inserted inside said elongated body, wherein said elongated body comprises a plurality of rigid elements aligned with each other and associated to one another by the interposition of spacer elements, substantially tubular in shape and coaxial to said elongated body, said rigid elements each including removable means for connecting to said extraction rod which are arranged inside said elongated body, and said spacer elements are comprised of one of an acrylic resin and a bone cement, wherein at least one of said rigid elements comprises at least one protrusion, protruding crossways to an axis of said elongated body, on which an edge of a distal end of one of said spacer elements at least partially rests, wherein said crossways protrusion comprises a discoidal body, substantially coaxial to said elongated body.

2. The equipment of claim 1, wherein said rigid elements are associated with said spacer elements by interposing a temporary fit-in type coupling.

3. The equipment of claim 2, wherein said temporary fit-in type coupling is suitable for connecting said rigid elements and said spacer elements as long as there is no axial separation force exerted between them of an established extent.

4. The equipment of claim 1, wherein at least one of said rigid elements comprises at least one connecting link, substantially tubular in shape, which can be fitted to said spacer elements.

5. The equipment of claim 4, wherein each connecting link can be fitted inside said spacer elements.

6. The equipment of claim 4, wherein at least one of said rigid elements features a pair of said at least one connecting link positioned at opposite axial ends.

7. The equipment of claim 4, wherein the rigid element arranged at a distal end of said elongated body features just one of said at least one connecting link.

8. The equipment of claim 1, wherein the rigid element arranged at a distal end of said elongated body features a closed bottom wall.

9. The equipment of claim 8, wherein an outer surface of said closed bottom wall is substantially pointed.

10. The equipment of claim 8, wherein an outer surface of said closed bottom wall is substantially conical in shape.

11. The equipment of claim 1, wherein said elongated body comprises attaching means to the cement.

12. The equipment of claim 11, wherein said attaching means is of the adhesive type.

13. The equipment of claim 11, wherein said attaching means comprises said spacer elements being made of a material that adheres to said cement.

14. The equipment of claim 13, wherein said material comprises polymethylacrylate.

15. The equipment of claim 1, wherein said means for connecting is of the threaded type.

16. The equipment of claim 15, wherein said means for connecting comprises an internal screw thread which is formed in said rigid elements and able to be engaged by a thread at least formed on at least a distal end of said extraction rod.

17. The equipment of claim 16, wherein said internal screw threads are substantially coaxial to said elongated body.

18. The equipment of claim 16, wherein a length of said thread is substantially less than a distance between at least two consecutive of said internal screw threads.

* * * * *